(12) United States Patent
O'Meadhra et al.

(10) Patent No.: US 7,674,931 B1
(45) Date of Patent: Mar. 9, 2010

(54) METHOD FOR PRODUCING 2,2,4-TRIMETHYL-1,3-PENTANEDIOL DI-2-ETHYLHEXANOATE

(75) Inventors: Ruairi Seosamh O'Meadhra, Kingsport, TN (US); Elden Mills Bailey, II, Blountville, TN (US); Steven Leroy Cook, Kingsport, TN (US); Phillip Wayne Turner, Blountville, TN (US)

(73) Assignee: Eastman Chemical Company, Kingsport, TN (US)

( * ) Notice: Subject to any disclaimer, the term of this patent is extended or adjusted under 35 U.S.C. 154(b) by 3 days.

(21) Appl. No.: 12/335,092

(22) Filed: Dec. 15, 2008

(51) Int. Cl.
*C07C 67/08* (2006.01)
(52) U.S. Cl. .................................... 560/263
(58) Field of Classification Search ............ None
See application file for complete search history.

(56) References Cited

U.S. PATENT DOCUMENTS 2,625,563 A * 1/1953 Bell .......................... 560/263
4,687,843 A * 8/1987 Smolin et al. .............. 536/18.3

FOREIGN PATENT DOCUMENTS

WO        WO 94/17028        8/1994

* cited by examiner

*Primary Examiner*—Paul A Zucker
(74) *Attorney, Agent, or Firm*—Brett L. Nelson; Bernard J. Graves, Jr.

(57) ABSTRACT

A method for maximizing the yield of 2,2,4-trimethyl-1,3-pentanediol di-2-ethylhexanoate (TMPD di-2-ethylhexanoate) from the reaction of 2,2,4-trimethyl-1,3-pentanediol (TMPD Glycol) and 2-ethylhexanoic acid through the intermediate compound 2,2,4-Trimethyl-1,3-pentanediol-2-ethylhexanoate (TMPD mono-2-ethylhexanoate) is disclosed. The method involves maintaining a water level in the reactor of at least 0.10 weight %, and preferable above 0.20 weight %, thereby reducing formation of 2,2,4-trimethylpent-3-enyl-2-ethylhexanoate, an undesirable by-product.

15 Claims, 2 Drawing Sheets

METHOD FOR PRODUCING 2,2,4-TRIMETHYL-1,3-PENTANEDIOL DI-2-ETHYLHEXANOATE

This invention relates to a method for preparing 2,2,4-trimethyl-1,3-pentanediol di-2-ethylhexanoate which includes controlling the water content of the reaction.

BACKGROUND OF THE INVENTION

The esterification of 2-ethylhexanoic acid with TMPD di-2-ethylhexanoate forms the diester TMPD di-2-ethylhexanoate and water (see FIG. 1). An intermediate monoester (TMPD mono-2-ethylhexanoate) is formed during the reaction, which is subsequently converted to the diester (shown in FIG. 2). In order to achieve reasonable production rates, the reaction is conducted in the temperature range of 190° C. to 210° C. At 200° C., it takes approximately 24 hours to fully complete the conversion of the reactants to the product. Due to the slow rate of the reaction, it can be said that it is controlled by the thermodynamic rates of the system and not by any mass or heat transfer limitations.

For esterifications of this type, it is customary to accelerate the reaction by adding an excess of one of the reactants. For the reaction described above, 100% excess 2-ethylhexanoic acid is added to the reactor. The reaction can also be accelerated by continuously removing water from the system, thus taking advantage of Le Chatelier's principal to drive the reaction in the forward direction. This is done by sparging nitrogen through the reactor to absorb and remove water from the vessel. A third way of increasing rates is by increasing the temperature of the reaction. It was found that the reaction was accompanied by a degradation mechanism which produced large quantities of the dehydrated monoester (shown in FIG. 3). The formation of this dehydrated monoester presents several problems. Firstly, a yield loss problem exists making it necessary to use more reactants to produce a unit of product. Secondly, a separation problem necessitates separation of the dehydrated monoester from the product before it can be sold. Thirdly, it was further found that the rate of formation of the dehydrated monoester is more sensitive to temperature than the main reaction. Thus, one of the key variables to increase the rate of reaction had to be moderated in order to minimize degradation yield loss. The present invention seeks to overcome these problems.

SUMMARY OF THE INVENTION

The present invention is directed to a method for producing 2,2,4-trimethyl-1,3-pentanediol di-2-ethylhexanoate, comprising:

reacting 2,2,4-trimethyl-1,3-pentanediol glycol and 2-ethylhexanoic acid to form 2,2,4-trimethyl-1,3-pentanediol di-2-ethylhexanoate, wherein a water concentration is maintained at about 0.1 weight percent or greater.

DETAILED DESCRIPTION

Figure 1:
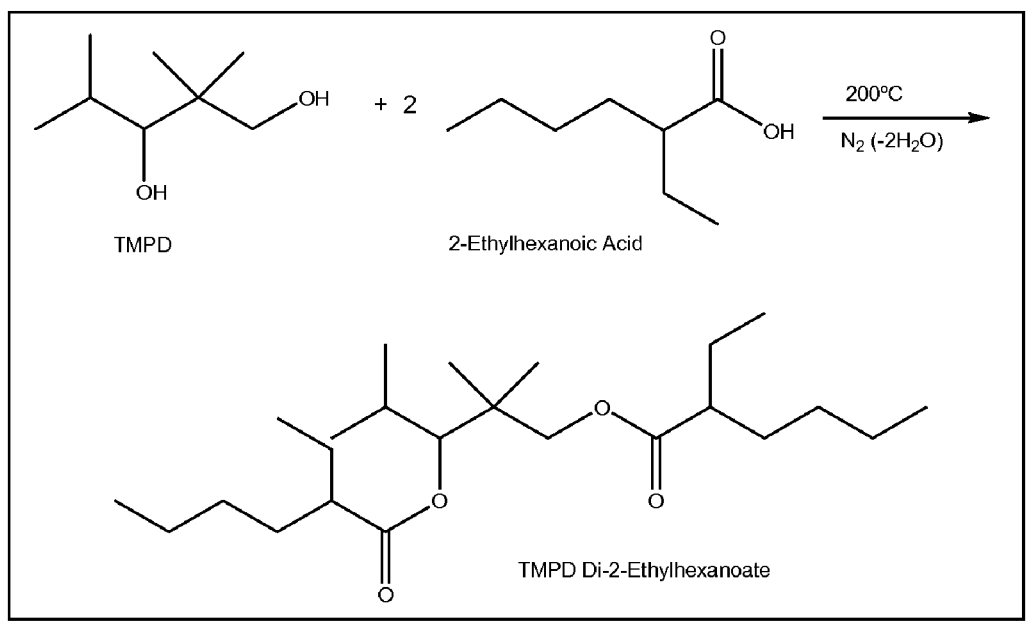
FIG. 1 shows an esterification reaction whereby 2 moles of 2-ethylhexanoic acid react with 1 mole of TMPD di-2-ethylhexanoate to form one mole of a diester (TMPD di-2-ethylhexanoate) and 2 moles of water.
Figure 2:
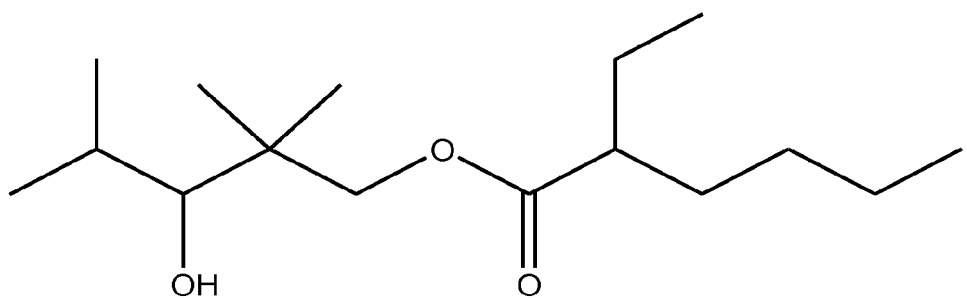
FIG. 2 shows the monoester 2,2,4-Trimethyl-1,3-pentanediol-2-ethylhexanoate.
Figure 3:
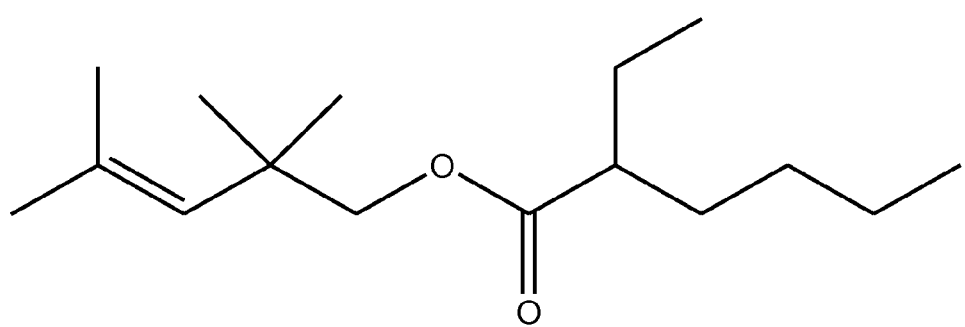
FIG. 3 shows dehydrated monoester 2,2,4-Trimethylpent-3-enyl-2-ethylhexanoate.

The present invention relates to a method for preparing 2,2,4-trimethyl-1,3-pentanediol di-2-ethylhexanoate which includes controlling the water content of the reaction. Moreover, the present invention seeks to overcome the problems associated with the esterification of 2-ethylhexanoic acid with TMPD di-ethylhexanoate, by maintaining the water content concentration in the reactor of between about 0.10 weight percent and about 0.50 weight percent. The detailed embodiments of this invention allow this product to be produced with very good overall yield and excellent carbon efficiency and with a minimum of unwanted byproducts.

In one embodiment, the invention concerns a process wherein 2,2,4-trimethyl-1,3-pentanediol (TMPD) is reacted with excess 2-ethylhexanoic acid with an initial inert gas sparge, such as dry nitrogen to initially drive off the water of reaction. Other mechanisms for removing water, such as stripping water with a low boiling solvent or employing a fractionation column, can be used. The amount of excess 2-ethylhexanoic acid above the theoretical minimum of two equivalents per equivalent of TMPD is within the range about 5 mole percent to about 200 mole percent. The sparge gas flow rate is maintained within about 0 cc/min to about 400 cc/min per liter of reactant volume, from about 10 CC/min to about 200 CC/min per liter, or even from about 25 CC/min to about 100 cc/min per liter. Typically the nitrogen purge is higher during the initial reaction period to remove accumulating water, but is slowed later as water generation tails off and approaches the minimum required to suppress dehydration. At a later stage of reaction the sparge can be discontinued in order to maintain the proper water concentration in the reaction mixture.

The desired reaction temperature is in the range of about 195° C. to about 250° C., about 220° C. to about 245° C., or about 230° C. to about 240° C. As higher reaction temperatures are used the reaction rate and thus productivity can increase. Moreover, as higher temperatures are used, higher pressure and lower nitrogen purge rates may be employed in order to maintain optimal levels of water. Maintenance of a water concentration in the reaction medium in a range of about 0.10 weight percent to about 0.50 weight percent enables minimization of an undesirable dehydration reaction which leads to formation of the unsaturated monoester 2,2,4-triethylpent-3-enyl-2-ethylexanoate. The water concentration can also be maintained in a range of about 0.10 weight percent to about 0.40 weight percent, or in a range of about 0.20 weight percent to about 0.30 weight percent. The reaction is continued until a target concentration of the desired 2,2,4-trimethyl-1,3-pentanediol di-2-ethylhexanoate (TMPD di-2-ethylhexanoate) is produced. Production of the unsaturated monoester is sufficiently low that the intermediate monoester of TMPD can be isolated by distillation and returned to the next cycle of the process. The process can be practiced in either a batch or continuous mode. In the continuous mode, a staged series of reactors is desirable to allow more complete conversion to the diester product. The process can be operated at atmospheric pressure or at reduced pressure.

The process described above can be operated at a pressure of from about 200 Torr to about 760 Torr, from about 300 Torr to about 600 Torr, or even from about 400 Torr to about 500 Torr. Pressure can be increased if water content is close to the maximum described above, in order to suppress further evaporation of the remaining water. Operating at different pressure does not have any inherent advantage from the reaction point of view other than aiding in water removal. According to an embodiment of the present invention, the process can be reacted for from about 5.0 hours to about 17 hours, from about 7.0 hours to about 14 hours, or even from about 9.0 to about 11.0 hours. To reach high conversion levels of the TMPD, such as 90%, 95% or even 98% or higher, the reaction time will vary according to operation temperature, pressure, and purge rate. Typically the reaction is conducted free of additional solvent. However, any low viscosity inert solvent could be added to the system if desired.

EXAMPLES

The present invention can be further illustrated in greater detail by the specific examples presented below. It is to be understood that these examples are illustrative embodiments and are not intended to be limiting of the invention, but rather are to be construed broadly within the scope and content of the appended claims. All parts and percentages in the examples are on a weight percent basis unless otherwise stated. The description in Example 1 gives a typical batch procedure for how 2,2,4-trimethyl-1,3-pentanediol di-2-ethylhexanoate (TMPD di-2-ethylhexanoate) is produced by reaction of TMPD Glycol and 2-ethylhexanoic acid. In Example 1, measures are taken to remove as much water as possible from the system, by both operating under a vacuum of 270 mmHg and by having a high sparge rate of nitrogen (200 cc/min) through the system. In Examples 2 and 3, a similar procedure was followed but the pressure and rate of nitrogen sparge were changed. A summary of the conditions is given in Table 1, along with the range of water concentrations in the reactor during a typical experiment and the amount of dehydrated monoester formed at the end of each experiment.

TABLE 1

Experimental conditions for experiments in Examples 1, 2 and 3.

| Ex. | Pressure [mmHg] | Temp. [Deg C.] | Nitrogen rate [cc/min] | Min water [wt %] | Max water [wt %] | Average water [wt %] | Time [hrs] | Dehydrated monoester [wt %] | Mono-ester [wt %] | Di-ester [wt %] |
|---|---|---|---|---|---|---|---|---|---|---|
| 1 | 270 | 198.34 | 200 | 0.05 | 0.09 | 0.07 | 6.65 | 0.77 | 25.14 | 14.51 |
| 2 | 300 | 199.02 | 200 | 0.04 | 0.09 | 0.05 | 7.5 | 2.01 | 21.85 | 21.44 |
| 3 | 760 | 195.50 | 50 | 0.2 | 0.58 | 0.42 | 8.4 | 0.01 | 25.41 | 16.53 |

The water content in Examples 1 and 2 are almost identical reflecting the similar conditions of both experiments. The concentration of dehydrated monoester at the end of each experiment was 0.77 weight % and 2.01 weight % respectively. In response to the higher pressure and lower nitrogen sparge rate in Example 3, the water content in solution is higher than in either Example 1 or 2. The amount of dehydrated monoester formed in Example 3 is also much lower than in Examples 1 and 2. Small differences in the extent of concentrations of mono- and di-ester can be seen between these experiments that are explained by the temperature profile followed by each experiment, especially during the initial 2 hours of each experiment.

In Table 2, the conditions and some results from Examples 4 to 8 are summarized. All of the experiments were done under atmospheric pressure as it was learned from Example 3 that sufficient water could be removed from the system at this pressure using a nitrogen sparge rate of 50 cc/min. The only exception in Table 2 is Example 4 which had a sparge rate of 200 cc/min. In Examples 7 and 8, the nitrogen sparge was stopped after 2 and 1 hours respectively as it was noticed that the water content was below 0.15 weight %. Except for Example 6 (8.42 hours), all of the examples in Table 2 had a much longer duration than the examples shown in Table 1. Also shown in Table 2 are the concentrations of the monoester and the diester at the end of each experiment.

TABLE 2

Experimental conditions for experiments in Examples 4, 5, 6, 7 and 8

| Ex. | Pressure [mmHg] | Temp. [Deg C.] | Nitrogen rate [cc/min] | Min water [wt %] | Max water [wt %] | Average water [wt %] | Time [hrs] | Dehydrated monoester [wt %] | Mono-ester [wt %] | Di-ester [wt %] |
|---|---|---|---|---|---|---|---|---|---|---|
| 4 | 760 | 199.37 | 200 | 0.13 | 0.40 | 0.24 | 18.58 | 0.25 | 12.261 | 25.76 |
| 5 | 760 | 207.97 | 50 | 0.14 | 0.32 | 0.21 | 17.5 | 0.38 | 9.641 | 29.15 |
| 6 | 760 | 216.96 | 50 | 0.00 | 0.38 | 0.18 | 8.42 | 0.68 | 14.338 | 21.24 |
| 7 | 760 | 225.74 | 50 (2 hrs) | 0.15 | 0.76 | 0.23 | 17.53 | 1.36 | 1.896 | 32.23 |
| 8 | 760 | 236.23 | 50 (1 hrs) | 0.01 | 0.21 | 0.10 | 16.91 | 3.31 | 0.674 | 36.57 |

In Example 4, after 18.58 hours, the dehydrated monoester content was 0.25 wt %. The average water concentration in this example was 0.24%. In Example 5, after 17.50 hours, the dehydrated monoester content was 0.38 wt %. The average water concentration in this example was 0.21%. The results from Examples 4 and 5 compare very favorably with the data in Examples 1 and 2 even though the reaction times are much longer and the average temperatures are higher.

Example 7 shows that operating at 225.74° C. for 17.53 hours, with an average water concentration of 0.23%, the dehydrated monoester concentration had reached a concentration of 1.36 weight %. Again, this compares very favorably with data from Example 1 and 2.

In general, the results in Table 2 show that the formation rate of dehydrated monoester is a function of temperature, but it also demonstrates that maintaining water at concentrations above 0.10% can significantly suppress the formation rate of the dehydrated monoester when compared to the data in Table 1.

Example 1

To a 3.8 liter jacketed vessel, 424 grams of 2,2,4-trimethyl-1,3-pentanediol (TMPD Glycol) were charged and heated to a nominal temperature of 150° C. When the TMPD Glycol began to melt, the agitator was switched on to a speed of 400 rpm. In a separate vessel, 1674 grams of 2-ethylhexanoic acid (2-EH) was heated. When the temperature of the 2-EH reached 175° C., it was added to the TMPD Glycol forming a clear solution. The solution was heated until it reached 200° C. The temperature of the vessel contents was controlled by manipulating the temperature of the fluid in the vessel jacket. A sparge of nitrogen was established through a small pipe that discharged 200 cc/min of nitrogen to the base of the vessel under the impeller. The pressure of the vessel was reduced to 270 mmHg to aid water removal from the vessel. A condenser located in the line between the vessel and the vacuum pump condensed any vapors in the gas and was collected in a receiver vessel where it separated into an aqueous and organic layer. The organic layer comprising mainly 2-EH was returned to the vessel while the water layer was removed from the system. During the experiment, samples of the solution were taken at discrete intervals to monitor the progress of the reaction. The results of this experiment are shown in Table 3.

TABLE 3

Experimental results for example 1

| Sample Number | | X29262-062-4 | X29262-062-7 | X29262-062-10 | X29262-062-16 | X29262-062-19 | X29262-062-22 | X29262-062-25 | X29262-062-28 |
|---|---|---|---|---|---|---|---|---|---|
| Time [hours] | 0 | 1.15 | 1.65 | 2.15 | 3.15 | 3.65 | 4.65 | 5.65 | 6.65 |
| Temp. [deg C.] | 150 | 193.73 | 198.04 | 199.07 | 198.98 | 199.17 | 199.74 | 199.36 | 198.63 |
| 2-Ethylhexanoic acid/TMPD | 100 | 87.20 | 82.52 | 78.78 | 71.86 | 69.58 | 65.24 | 61.70 | 58.95 |
| Dehydrated monoester | 0 | 0.03 | 0.07 | 0.11 | 0.26 | 0.32 | 0.49 | 0.62 | 0.77 |
| TMPD 2-EH monoester | 0 | 11.26 | 15.11 | 17.92 | 22.17 | 23.25 | 24.74 | 25.30 | 25.14 |
| TMPD -2EH Diester | 0 | 1.17 | 1.91 | 2.78 | 5.21 | 6.30 | 8.97 | 11.78 | 14.51 |
| Water | 0 | 0.06 | 0.05 | 0.09 | 0.07 | 0.06 | 0.06 | 0.07 | 0.06 |

Example 2

To a 3.8 liter jacketed vessel, 424 grams of 2,2,4-trimethyl-1,3-pentanediol (TMPD Glycol) were charged and heated to a nominal temperature of 150° C. When the TMPD Glycol began to melt, the agitator was switched on to a speed of 400 rpm. In a separate vessel, 1674 grams of 2-ethylhexanoic acid (2-EH) was heated. When the temperature of the 2-EH reached 175° C., it was added to the TMPD Glycol forming a clear solution. The solution was heated until it reached 200° C. The temperature of the vessel contents was controlled by manipulating the temperature of the fluid in the vessel jacket. A sparge of nitrogen was established through a small pipe that discharged 200 cc/min of nitrogen to the base of the vessel under the impeller. The pressure of the vessel was reduced to 300 mmHg to aid water removal from the vessel. A condenser located in the line between the vessel and the vacuum pump condensed any vapors in the gas and was collected in a receiver vessel where it separated into an aqueous and water layer. The organic layer comprising mainly 2-EH was returned to the vessel while the water layer was removed from the system. During the experiment, samples of the solution were taken at discrete intervals to monitor the progress of the reaction. The results of this experiment are shown in Table 4.

TABLE 4

Experimental results for example 2

| Sample Number | | X29262-064-1 | X29262-064-4 | X29262-064-7 | X29262-064-10 | X29262-064-13 | X29262-064-16 | X29262-064-19 | X29262-064-22 | X29262-064-25 | X29262-064-28 |
|---|---|---|---|---|---|---|---|---|---|---|---|
| Time [hours] | 0 | 1.50 | 2.00 | 2.50 | 3.00 | 3.50 | 4.00 | 4.50 | 5.50 | 7.50 | 8.50 |
| Temperature [deg C.] | 150.00 | 196.88 | 199.00 | 199.09 | 198.98 | 199.07 | 199.37 | 199.71 | 199.45 | 199.27 | 199.36 |
| 2-Ethylhexanoic acid/TMPD | | 86.84 | 82.12 | 77.06 | 73.04 | 69.72 | 66.97 | 64.52 | 60.59 | 55.16 | 53.74 |
| Dehydrated monoester | | 0.05 | 0.12 | 0.29 | 0.46 | 0.63 | 0.81 | 0.98 | 1.35 | 2.01 | 2.21 |
| TMPD 2-EH monoester | | 11.61 | 15.58 | 19.10 | 21.47 | 23.05 | 23.94 | 24.55 | 24.70 | 22.93 | 21.85 |
| TMPD -2EH Diester | | 1.11 | 1.77 | 3.10 | 4.58 | 6.09 | 7.73 | 9.39 | 12.73 | 19.18 | 21.44 |
| Water | | 0.06 | 0.08 | 0.04 | 0.06 | 0.04 | 0.04 | 0.06 | 0.05 | 0.05 | 0.05 |

Example 3

To a 3.8 liter jacketed vessel, 424 grams of 2,2,4-trimethyl-1,3-pentanediol (TMPD Glycol) were charged and heated to a nominal temperature of 150° C. When the TMPD Glycol began to melt, the agitator was switched on to a speed of 400 rpm. In a separate vessel, 1674 grams of 2-ethylhexanoic acid (2-EH) was heated. When the temperature of the 2-EH reached 175° C., it was added to the TMPD Glycol forming a clear solution. The solution was heated until it reached 200° C. The temperature of the vessel contents was controlled by manipulating the temperature of the fluid in the vessel jacket. A sparge of nitrogen was established through a small pipe that discharged 50 cc/min of nitrogen to the base of the vessel under the impeller. The pressure of the vessel was atmospheric (760 mmHg). A condenser located in the line between the vessel and the vacuum pump condensed any vapors in the gas and was collected in a receiver vessel where it separated into an aqueous and water layer. The organic layer comprising mainly 2-EH was returned to the vessel while the water layer was removed from the system. During the experiment, samples of the solution were taken at discrete intervals to monitor the progress of the reaction. The results of this experiment are shown in Table 5.

Example 4

To a 3.8 liter jacketed vessel, 424 grams of 2,2,4-trimethyl-1,3-pentanediol (TMPD Glycol) were charged and heated to a nominal temperature of 150° C. When the TMPD Glycol began to melt, the agitator was switched on to a speed of 400 rpm. In a separate vessel, 1674 grams of 2-ethylhexanoic acid (2-EH) was heated. When the temperature of the 2-EH reached 175° C., it was added to the TMPD Glycol forming a clear solution. The solution was heated until it reached 200° C. The temperature of the vessel contents was controlled by manipulating the temperature of the fluid in the vessel jacket. A sparge of nitrogen was established through a small pipe that discharged 200 cc/min of nitrogen to the base of the vessel under the impeller. The pressure of the vessel was atmospheric (760 mmHg). A condenser located in the line between the vessel and the vacuum pump condensed any vapors in the gas and was collected in a receiver vessel where it separated into an aqueous and water layer. The organic layer comprising mainly 2-EH was returned to the vessel while the water layer was removed from the system. During the experiment, samples of the solution were taken at discrete intervals to monitor the progress of the reaction. The results of this experiment are shown in Table 6.

TABLE 5

Experimental Results for example 3

| Sample Number | | X29262-068-1 | X29262-068-3 | X29262-068-5 | X29262-068-7 | X29262-064-9 | X29262-064-11 |
|---|---|---|---|---|---|---|---|
| Time [hours] | 0 | 0.40 | 0.90 | 1.40 | 1.90 | 2.40 | 2.90 |
| Temperature [deg C.] | 149.99 | 169.41 | 188.03 | 196.05 | 198.69 | 199.11 | 198.99 |
| 2-Ethylhexanoic acid/TMPD | | 97.69 | 93.31 | 88.87 | 84.31 | 79.76 | 76.88 |
| Dehydrated monoester | | 0.00 | 0.00 | 0.00 | 0.01 | 0.02 | 0.02 |
| TMPD 2-EH monoester | | 1.98 | 6.14 | 10.21 | 14.08 | 17.61 | 19.60 |
| TMPD -2EH Diester | | 0.04 | 0.20 | 0.60 | 1.26 | 2.25 | 3.09 |
| Water | 0 | 0.20 | 0.40 | 0.52 | 0.28 | 0.42 | 0.33 |

| Sample Number | X29262-064-13 | X29262-064-15 | X29262-064-17 | X29262-064-19 | X29262-064-21 | X29262-064-23 |
|---|---|---|---|---|---|---|
| Time [hours] | 3.40 | 4.40 | 5.40 | 6.40 | 7.40 | 8.40 |
| Temperature [deg C.] | 199.03 | 199.67 | 199.52 | 198.70 | 199.13 | 199.67 |
| 2-Ethylhexanoic acid/TMPD | 73.88 | 68.56 | 64.97 | 62.11 | 59.41 | 57.33 |
| Dehydrated monoester | 0.00 | 0.05 | 0.07 | 0.09 | 0.11 | 0.01 |
| TMPD 2-EH monoester | 21.48 | 24.20 | 25.39 | 25.72 | 25.73 | 25.41 |
| TMPD -2EH Diester | 4.18 | 6.69 | 9.03 | 11.51 | 14.12 | 16.53 |
| Water | 0.48 | 0.31 | 0.37 | 0.79 | 0.58 | 0.39 |

TABLE 6

Experimental Results for example 4

| Sample Number | | X29262-070-1 | X29262-070-3 | X29262-070-5 | X29262-070-7 | X29262-070-9 | X29262-070-11 | X29262-070-13 | X29262-070-15 |
|---|---|---|---|---|---|---|---|---|---|
| Time [hours] | 0 | 0.08 | 0.58 | 1.08 | 1.58 | 2.08 | 2.58 | 3.08 | 4.08 |
| Temperature [deg C.] | 177.21 | 177.21 | 193.68 | 200.09 | 201.43 | 200.82 | 199.99 | 199.68 | 200.66 |
| 2-Ethylhexanoic acid | 80.00 | 79.02 | 78.26 | 77.00 | 75.98 | 74.45 | 73.47 | 72.60 | 70.96 |
| TMPD | 20.00 | 19.20 | 17.15 | 14.88 | 12.86 | 10.93 | 9.44 | 8.21 | 6.14 |
| Dehydrated monoester | 0 | 0.00 | 0.01 | 0.01 | 0.01 | 0.02 | 0.03 | 0.04 | 0.05 |
| TMPD 2-EH monoester | 0 | 0.63 | 3.95 | 7.21 | 9.91 | 12.60 | 14.36 | 15.81 | 17.83 |
| TMPD -2EH Diester | 0 | 0.60 | 0.12 | 0.37 | 0.78 | 1.40 | 2.03 | 2.74 | 4.31 |
| Water | 0 | 0.14 | 0.36 | 0.23 | 0.25 | 0.32 | 0.33 | 0.24 | 0.26 |

| Sample Number | X29262-070-17 | X29262-070-19 | X29262-070-21 | X29262-070-23 | X29262-070-25 | X29262-070-13 | X29262-070-15 | X29262-070-17 |
|---|---|---|---|---|---|---|---|---|
| Time [hours] | 5.08 | 6.08 | 7.08 | 8.08 | 9.08 | 3.08 | 4.08 | 5.08 |
| Temperature [deg C.] | 201.78 | 201.37 | 200.45 | 201.17 | 201.29 | 199.68 | 200.66 | 201.78 |
| 2-Ethylhexanoic acid | 69.60 | 68.17 | 68.08 | 66.31 | 65.81 | 72.60 | 70.96 | 69.60 |
| TMPD | 4.55 | 3.39 | 2.62 | 2.06 | 1.56 | 8.21 | 6.14 | 4.55 |
| Dehydrated monoester | 0.07 | 0.10 | 0.11 | 0.12 | 0.14 | 0.04 | 0.05 | 0.07 |
| TMPD 2-EH monoester | 18.95 | 19.60 | 19.45 | 19.43 | 18.75 | 15.81 | 17.83 | 18.95 |
| TMPD -2EH Diester | 6.12 | 8.05 | 9.46 | 11.26 | 12.88 | 2.74 | 4.31 | 6.12 |
| Water | 0.28 | 0.31 | 0.29 | 0.32 | 0.40 | 0.24 | 0.26 | 0.28 |

| Sample Number | X29262-070-19 | X29262-070-21 | X29262-070-23 | X29262-070-25 | X29262-070-41 | X29262-070-43 | X29262-070-45 |
|---|---|---|---|---|---|---|---|
| Time [hours] | 6.08 | 7.08 | 8.08 | 9.08 | 16.58 | 17.58 | 18.58 |
| Temperature [deg C.] | 201.37 | 200.45 | 201.17 | 201.29 | 200.81 | 201.50 | 199.02 |
| 2-Ethylhexanoic acid | 68.17 | 68.08 | 66.31 | 65.81 | 61.31 | 60.98 | 60.65 |
| TMPD | 3.39 | 2.62 | 2.06 | 1.56 | 0.27 | 0.24 | 0.20 |
| Dehydrated monoester | 0.10 | 0.11 | 0.12 | 0.14 | 0.23 | 0.24 | 0.25 |
| TMPD 2-EH monoester | 19.60 | 19.45 | 19.43 | 18.75 | 13.46 | 12.86 | 12.26 |
| TMPD -2EH Diester | 8.05 | 9.46 | 11.26 | 12.88 | 23.95 | 24.86 | 25.76 |
| Water | 0.31 | 0.29 | 0.32 | 0.40 | 0.16 | 0.13 | 0.21 |

Example 5

To a 3.8 liter jacketed vessel, 424 grams of 2,2,4-trimethyl-1,3-pentanediol (TMPD Glycol) were charged and heated to a nominal temperature of 150° C. When the TMPD Glycol began to melt, the agitator was switched on to a speed of 400 rpm. In a separate vessel, 1674 grams of 2-ethylhexanoic acid (2-EH) was heated. When the temperature of the 2-EH reached 175° C., it was added to the TMPD Glycol forming a clear solution. The solution was heated until it reached 210° C. The temperature of the vessel contents was controlled by manipulating the temperature of the fluid in the vessel jacket. A sparge of nitrogen was established through a small pipe that discharged 50 cc/min of nitrogen to the base of the vessel under the impeller. The pressure of the vessel was atmospheric (760 mmHg). A condenser located in the line between the vessel and the vacuum pump condensed any vapors in the gas and was collected in a receiver vessel where it separated into an aqueous and water layer. The organic layer comprising mainly 2-EH was returned to the vessel while the water layer was removed from the system. During the experiment, samples of the solution were taken at discrete intervals to monitor the progress of the reaction. The results of this experiment are shown in Table 7.

TABLE 7

Experimental Results for example 5

| Sample Number | | X29262-072-1 | X29262-072-3 | X29262-072-5 | X29262-072-7 | X29262-072-9 | X29262-072-11 | X29262-072-13 |
|---|---|---|---|---|---|---|---|---|
| Time [hours] | 0 | 0.50 | 1.00 | 1.50 | 2.00 | 2.50 | 3.00 | 3.50 |
| Temperature [deg C.] | 175.66 | 193.03 | 201.42 | 204.43 | 205.99 | 206.30 | 206.67 | 207.30 |
| 2-Ethylhexanoic acid | 80.00 | 78.36 | 76.90 | 75.73 | 74.30 | 73.18 | 72.11 | 71.10 |
| TMPD | 20.00 | 18.08 | 15.29 | 13.12 | 10.78 | 9.21 | 7.66 | 6.45 |
| Dehydrated monoester | 0 | 0.01 | 0.02 | 0.02 | 0.03 | 0.04 | 0.05 | 0.07 |
| TMPD 2-EH monoester | 0 | 2.56 | 6.66 | 9.70 | 12.76 | 14.70 | 16.39 | 17.60 |
| TMPD -2EH Diester | 0 | 0.19 | 0.65 | 0.79 | 1.51 | 2.26 | 3.18 | 4.10 |
| Water | 0 | 0.27 | 0.26 | 0.25 | 0.26 | 0.21 | 0.22 | 0.22 |

| Sample Number | X29262-072-15 | X29262-072-17 | X29262-072-19 | X29262-072-21 | X29262-072-23 | X29262-072-25 | X29262-072-27 | X29262-072-29 |
|---|---|---|---|---|---|---|---|---|
| Time [hours] | 4.50 | 5.50 | 6.50 | 7.50 | 8.50 | 9.50 | 10.00 | 11.00 |
| Temperature [deg C.] | 209.37 | 210.55 | 210.31 | 209.73 | 210.24 | 210.00 | 210.00 | 210.00 |
| 2-Ethylhexanoic acid | 69.14 | 67.86 | 66.50 | 65.62 | 64.58 | 63.56 | 62.70 | 62.18 |

TABLE 7-continued

Experimental Results for example 5

| | | | | | | | |
|---|---|---|---|---|---|---|---|
| TMPD | 4.34 | 3.05 | 2.13 | 1.46 | 1.07 | 0.77 | 0.56 | 0.44 |
| Dehydrated monoester | 0.10 | 0.13 | 0.16 | 0.20 | 0.22 | 0.25 | 0.27 | 0.27 |
| TMPD 2-EH monoester | 19.23 | 19.56 | 18.45 | 18.71 | 18.03 | 17.06 | 15.85 | 15.02 |
| TMPD -2EH Diester | 6.48 | 8.66 | 10.99 | 13.41 | 15.34 | 17.32 | 19.50 | 20.90 |
| Water | 0.17 | 0.32 | 0.19 | 0.17 | 0.30 | 0.18 | 0.15 | 0.14 |

| Sample Number | X29262-072-31 | X29262-072-33 | X29262-072-35 | X29262-072-37 | X29262-072-39 | X29262-072-41 | X29262-072-43 |
|---|---|---|---|---|---|---|---|
| Time [hours] | 12.00 | 13.00 | 14.00 | 15.17 | 16.03 | 16.83 | 17.50 |
| Temperature [deg C.] | 210.00 | 210.00 | 210.00 | 210.00 | 210.00 | 210.00 | 210.00 |
| 2-Ethylhexanoic acid | 61.69 | 61.05 | 61.00 | 60.25 | 59.99 | 59.71 | 59.51 |
| TMPD | 0.35 | 0.27 | 0.22 | 0.17 | 0.15 | 0.13 | 0.13 |
| Dehydrated monoester | 0.30 | 0.31 | 0.33 | 0.35 | 0.36 | 0.37 | 0.38 |
| TMPD 2-EH monoester | 14.25 | 13.23 | 12.38 | 11.44 | 10.73 | 10.11 | 9.64 |
| TMPD -2EH Diester | 22.29 | 23.75 | 24.97 | 26.71 | 27.73 | 28.52 | 29.15 |
| Water | 0.15 | 0.20 | 0.22 | 0.19 | 0.21 | 0.35 | 0.29 |

Example 6

To a 3.8 liter jacketed vessel, 424 grams of 2,2,4-trimethyl-1,3-pentanediol (TMPD Glycol) were charged and heated to a nominal temperature of 150° C. When the TMPD Glycol began to melt, the agitator was switched on to a speed of 400 rpm. In a separate vessel, 1674 grams of 2-ethylhexanoic acid (2-EH) was heated. When the temperature of the 2-EH reached 175° C., it was added to the TMPD Glycol forming a clear solution. The solution was heated until it reached 220° C. The temperature of the vessel contents was controlled by manipulating the temperature of the fluid in the vessel jacket. A sparge of nitrogen was established through a small pipe that discharged 50 cc/min of nitrogen to the base of the vessel under the impeller. The pressure of the vessel was atmospheric (760 mmHg). A condenser located in the line between the vessel and the vacuum pump condensed any vapors in the gas and was collected in a receiver vessel where it separated into an aqueous and water layer. The organic layer comprising mainly 2-EH was returned to the vessel while the water layer was removed from the system. During the experiment, samples of the solution were taken at discrete intervals to monitor the progress of the reaction. The results of this experiment are shown in Table 8.

TABLE 8

Experimental Results for example 6

| Sample Number | | X29262-082-1 | X29262-082-3 | X29262-082-5 | X29262-082-7 | X29262-082-9 | X29262-082-11 |
|---|---|---|---|---|---|---|---|
| Time [hours] | 0 | 0.42 | 0.92 | 1.42 | 1.92 | 2.42 | 2.92 |
| Temperature [deg C.] | 180.41 | 195.75 | 208.19 | 215.33 | 218.97 | 220.48 | 220.81 |
| 2-Ethylhexanoic acid | 80 | 78.83 | 77.63 | 75.18 | 73.35 | 71.86 | 70.38 |
| TMPD | 20 | 17.74 | 15.61 | 11.66 | 8.91 | 6.90 | 5.20 |
| Dehydrated monoester | 0 | 0.00 | 0.00 | 0.03 | 0.08 | 0.13 | 0.20 |
| TMPD 2-EH monoester | 0 | 2.96 | 6.10 | 11.57 | 14.92 | 17.01 | 18.49 |
| TMPD -2EH Diester | 0 | 0.09 | 0.27 | 1.13 | 2.29 | 3.60 | 5.23 |
| Water | 0 | 0.38 | 0.25 | 0.16 | 0.15 | 0.16 | 0.21 |

| Sample Number | X29262-082-13 | X29262-082-15 | X29262-082-17 | X29262-082-19 | X29262-082-21 | X29262-082-23 |
|---|---|---|---|---|---|---|
| Time [hours] | 3.42 | 4.42 | 5.42 | 6.42 | 7.42 | 8.42 |
| Temperature [deg C.] | 220.63 | 220.19 | 220.47 | 221.19 | 221.44 | 220.09 |
| 2-Ethylhexanoic acid | 69.30 | 67.11 | 65.57 | 64.42 | 63.41 | 62.76 |
| TMPD | 3.99 | 2.27 | 1.34 | 0.86 | 0.55 | 0.36 |
| Dehydrated monoester | 0.26 | 0.38 | 0.48 | 0.55 | 0.62 | 0.68 |
| TMPD 2-EH monoester | 19.08 | 19.31 | 18.40 | 17.27 | 15.83 | 14.34 |
| TMPD -2EH Diester | 6.81 | 10.35 | 13.59 | 16.24 | 18.91 | 21.24 |
| Water | 0.19 | 0.13 | 0.12 | 0.12 | 0.11 | 0.13 |

Example 7

To a 3.8 liter jacketed vessel, 424 grams of 2,2,4-trimethyl-1,3-pentanediol (TMPD Glycol) were charged and heated to a nominal temperature of 150° C. When the TMPD Glycol began to melt, the agitator was switched on to a speed of 400 rpm. In a separate vessel, 1674 grams of 2-ethylhexanoic acid (2-EH) was heated. When the temperature of the 2-EH reached 175° C., it was added to the TMPD Glycol forming a clear solution. The solution was heated until it reached 230° C. The temperature of the vessel contents was controlled by manipulating the temperature of the fluid in the vessel jacket. A sparge of nitrogen was established through a small pipe that discharged 50 cc/min of nitrogen to the base of the vessel under the impeller. Nitrogen purging was discontinued after 2 hours of operation. The pressure of the vessel was atmospheric (760 mmHg). A condenser located in the line between the vessel and the vacuum pump condensed any vapors in the gas and was collected in a receiver vessel where it separated into an aqueous and water layer. The organic layer comprising mainly 2-EH was returned to the vessel while the water layer was removed from the system. During the experiment, samples of the solution were taken at discrete intervals to monitor the progress of the reaction. The results of this experiment are shown in Table 9.

TABLE 9

Experimental Results for example 7

| Sample Number | X29262-086-1 | X29262-086-3 | X29262-086-5 | X29262-086-7 | X29262-086-9 | X29262-086-11 |
|---|---|---|---|---|---|---|
| Time [hours] | 0 | 0.73 | 1.23 | 1.73 | 2.23 | 2.73 | 3.23 |
| Temperature [deg C.] | 179.84 | 203.24 | 214.78 | 222.42 | 226.87 | 228.97 | 229.58 |
| 2-Ethylhexanoic acid | 80 | 76.95 | 75.88 | 73.38 | 71.61 | 69.63 | 68.52 |
| TMPD | 20 | 16.17 | 13.56 | 9.72 | 7.05 | 4.69 | 3.45 |
| Dehydrated monoester | 0 | 0.00 | 0.01 | 0.08 | 0.18 | 0.34 | 0.44 |
| TMPD 2-EH monoester | 0 | 5.45 | 9.41 | 14.34 | 17.03 | 18.82 | 19.22 |
| TMPD -2EH Diester | 0 | 0.22 | 0.66 | 1.96 | 3.58 | 5.95 | 7.81 |
| Water | 0 | 0.36 | 0.22 | 0.18 | 0.15 | 0.17 | 0.19 |

| Sample Number | X29262-086-13 | X29262-086-15 | X29262-086-17 | X29262-086-19 | X29262-086-21 | X29262-086-23 | X29262-086-25 |
|---|---|---|---|---|---|---|---|
| Time [hours] | 3.73 | 4.73 | 5.73 | 6.73 | 7.73 | 8.73 | 10.53 |
| Temperature [deg C.] | 229.47 | 229.26 | 230.52 | 232.06 | 230.96 | 176.39 | 228.98 |
| 2-Ethylhexanoic acid | 67.37 | 68.17 | 63.79 | 63.10 | 61.97 | 61.29 | 64.93 |
| TMPD | 2.44 | 1.27 | 0.65 | 0.35 | 0.20 | 0.14 | 0.07 |
| Dehydrated monoester | 0.54 | 0.70 | 0.92 | 1.08 | 1.19 | 1.26 | 1.14 |
| TMPD 2-EH monoester | 19.13 | 16.43 | 16.06 | 13.88 | 11.85 | 10.72 | 6.95 |
| TMPD -2EH Diester | 9.90 | 12.83 | 17.99 | 20.96 | 24.16 | 25.94 | 26.12 |
| Water | 0.19 | 0.76 | 0.15 | 0.28 | 0.15 | 0.18 | 0.20 |

| Sample Number | X29262-086-27 | X29262-086-29 | X29262-086-31 | X29262-086-33 | X29262-086-35 | X29262-086-37 | X29262-086-39 |
|---|---|---|---|---|---|---|---|
| Time [hours] | 11.53 | 12.53 | 13.53 | 14.53 | 15.53 | 16.53 | 17.53 |
| Temperature [deg C.] | 231.41 | 230.91 | 231.23 | 232.71 | 234.55 | 235.73 | 234.6969 |
| 2-Ethylhexanoic acid | 65.43 | 64.91 | 64.67 | 64.78 | 63.64 | 64.33 | 63.87 |
| TMPD | 0.05 | 0.03 | 0.03 | 0.02 | 0.02 | 0.00 | 0.00 |
| Dehydrated monoester | 1.17 | 1.23 | 1.26 | 1.28 | 1.36 | 1.33 | 1.36 |
| TMPD 2-EH monoester | 5.71 | 4.56 | 3.94 | 3.24 | 2.78 | 2.22 | 1.90 |
| TMPD -2EH Diester | 27.03 | 28.64 | 29.49 | 30.08 | 31.54 | 31.46 | 32.23 |
| Water | 0.20 | 0.20 | 0.20 | 0.20 | 0.20 | 0.20 | 0.20 |

Example 8

To a 3.8 liter jacketed vessel, 424 grams of 2,2,4-trimethyl-1,3-pentanediol (TMPD Glycol) were charged and heated to a nominal temperature of 150° C. When the TMPD Glycol began to melt, the agitator was switched on to a speed of 400 rpm. In a separate vessel, 1674 grams of 2-ethylhexanoic acid (2-EH) was heated. When the temperature of the 2-EH reached 175° C., it was added to the TMPD Glycol forming a clear solution. The solution was heated until it reached 240° C. The temperature of the vessel contents was controlled by manipulating the temperature of the fluid in the vessel jacket. A sparge of nitrogen was established through a small pipe that discharged 50 cc/min of nitrogen to the base of the vessel under the impeller. Nitrogen purging was discontinued after 1 hours of operation. The pressure of the vessel was atmospheric (760 mmHg). A condenser located in the line between the vessel and the vacuum pump condensed any vapors in the gas and was collected in a receiver vessel where it separated into an aqueous and water layer. The organic layer comprising mainly 2-EH was returned to the vessel while the water layer was removed from the system. During the experiment, samples of the solution were taken at discrete intervals to monitor the progress of the reaction. The results of this experiment are shown in Table 10.

TABLE 10

Experimental Results for example 8

| Sample Number | X29262-088-1 | X29262-088-3 | X29262-088-5 | X29262-088-7 | X29262-088-9 | X29262-088-11 |
|---|---|---|---|---|---|---|
| Time [hours] | 0 | 0.79 | 1.29 | 1.79 | 2.29 | 2.79 | 3.29 |
| Temperature [deg C.] | 177.67 | 209.27 | 222.07 | 229.87 | 234.47 | 237.05 | 238.33 |
| 2-Ethylhexanoic acid | 80 | 76.63 | 74.97 | 72.30 | 70.19 | 68.30 | 66.73 |
| TMPD | 20 | 15.43 | 11.80 | 7.90 | 5.26 | 3.38 | 2.00 |
| Dehydrated monoester | 0 | 0.01 | 0.00 | 0.25 | 0.54 | 0.89 | 1.27 |
| TMPD 2-EH monoester | 0 | 6.93 | 11.51 | 15.98 | 18.04 | 18.70 | 18.05 |
| TMPD -2EH Diester | 0 | 0.00 | 1.21 | 3.02 | 5.46 | 8.19 | 11.38 |
| Water | 0 | 0.21 | 0.11 | 0.08 | 0.07 | 0.07 | 0.09 |

| Sample Number | X29262-088-13 | X29262-088-15 | X29262-088-17 | X29262-088-19 | X29262-088-21 | X29262-088-23 | X29262-088-25 |
|---|---|---|---|---|---|---|---|
| Time [hours] | 3.79 | 4.79 | 5.79 | 6.79 | 7.79 | 8.79 | 9.79 |
| Temperature [deg C.] | 238.80 | 238.48 | 238.07 | 239.19 | 241.69 | 239.93 | 216.73 |
| 2-Ethylhexanoic acid | 65.82 | 64.16 | 62.92 | 62.81 | 60.98 | 62.35 | 59.31 |
| TMPD | 1.29 | 0.62 | 0.27 | 0.13 | 0.06 | 0.04 | 0.03 |
| Dehydrated monoester | 1.56 | 1.99 | 2.38 | 2.65 | 2.99 | 3.05 | 3.20 |
| TMPD 2-EH monoester | 16.87 | 14.66 | 12.83 | 9.13 | 7.26 | 5.48 | 4.59 |
| TMPD -2EH Diester | 13.86 | 17.92 | 21.93 | 24.61 | 28.03 | 27.40 | 32.04 |
| Water | 0.13 | 0.12 | 0.07 | 0.10 | 0.07 | 0.20 | 0.03 |

| Sample Number | X29262-088-27 | X29262-088-29 | X29262-088-31 | X29262-088-33 | X29262-088-35 | X29262-088-37 | X29262-088-39 |
|---|---|---|---|---|---|---|---|
| Time [hours] | 10.91 | 11.91 | 12.91 | 13.91 | 14.91 | 15.91 | 16.91 |
| Temperature [deg C.] | 236.75 | 243.87 | 243.87 | 243.19 | 243.68 | 245.16 | 244.12 |
| 2-Ethylhexanoic acid | 59.60 | 59.53 | 59.10 | 64.37 | 60.11 | 59.60 | 58.51 |
| TMPD | 0.03 | 0.01 | 0.00 | 0.01 | 0.02 | 0.00 | 0.01 |
| Dehydrated monoester | 3.17 | 3.25 | 3.34 | 3.13 | 3.31 | 3.27 | 3.31 |
| TMPD 2-EH monoester | 3.99 | 2.92 | 2.08 | 1.34 | 1.17 | 0.82 | 0.67 |
| TMPD -2EH Diester | 32.44 | 33.53 | 34.61 | 30.38 | 34.62 | 35.42 | 36.57 |
| Water | 0.06 | 0.05 | 0.01 | 0.15 | 0.19 | 0.07 | 0.12 |

Having described the invention in detail, those skilled in the art will appreciate that modifications may be made to the various aspects of the invention without departing from the scope and spirit of the invention disclosed and described herein. It is, therefore, not intended that the scope of the invention be limited to the specific embodiments illustrated and described but rather it is intended that the scope of the present invention be determined by the appended claims and their equivalents.

What is claimed is:

1. A method for producing 2,2,4-trimethyl-1,3-pentanediol di-2-ethylhexanoate, comprising:
    reacting 2,2,4-trimethyl-1,3pentanediol glycol and 2-ethylhexanoic acid to produce 2,2,4-trimethyl-1,3-pentanediol di-2-ethylhexanoate in the presence of water of reaction,
    wherein the water concentration is maintained at about 0.1 weight percent or greater.

2. The method according to claim 1, wherein said water concentration is maintained at about 0.10 weight percent to about 0.40 weight percent.

3. The method according to claim 2, wherein said water concentration is maintained at about 0.20 weight percent to about 0.30 weight percent.

4. The method according to claim 1, wherein the water concentration is maintained via an inert sparge gas.

5. The method according to claim 4, wherein the sparge gas is nitrogen.

6. The method according to claim 4, wherein the sparge gas flow rate is maintained at a rate of from about 0 cc/min to about 400 cc/min per liter of reactant volume.

7. The method according to claim 6, wherein the sparge gas flow rate is maintained at a rate of from about 10 CC/min to about 200 CC/min per liter.

8. The method according to claim 7, wherein the sparge gas flow rate is maintained at a rate of from about 25 CC/min to about 100 cc/min per liter.

9. The method according to claim 1, wherein said reacting is at a temperature of from about 195° C. to about 250° C.

10. The method according to claim 9, wherein said temperature is from about 220° C. to about 245° C.

11. The method according to claim 10, wherein said temperature is from about 230° C. to about 240° C.

12. The method according to claim 1, wherein said reacting is at a pressure of from about 200 Torr to about 760 Torr.

13. The method according to claim 12, wherein said reacting is at a pressure of from about 300 Torr to about 600 Torr.

14. The method according to claim 13, wherein said reacting is at a pressure of from about 400 Torr to about 500 Torr.

15. The method according to claim 1, wherein the method is a batch method or continuous mode method.

* * * * *